United States Patent
Sato

(10) Patent No.: US 7,075,657 B2
(45) Date of Patent: Jul. 11, 2006

(54) SURFACE PLASMON RESONANCE MEASURING APPARATUS

(75) Inventor: Shu Sato, Kaisei-machi (JP)

(73) Assignee: Fuji Photo Film Co., Ltd., Kanagawa-ken (JP)

(*) Notice: Subject to any disclaimer, the term of this patent is extended or adjusted under 35 U.S.C. 154(b) by 0 days.

(21) Appl. No.: 10/648,509

(22) Filed: Aug. 27, 2003

(65) Prior Publication Data
US 2004/0042012 A1 Mar. 4, 2004

(30) Foreign Application Priority Data

| Aug. 28, 2002 | (JP) | ............................ 2002-249684 |
| Aug. 30, 2002 | (JP) | ............................ 2002-254727 |
| Sep. 30, 2002 | (JP) | ............................ 2002-287291 |

(51) Int. Cl.
*G01N 21/55* (2006.01)

(52) U.S. Cl. ...................... 356/455; 356/446; 356/447; 356/448; 356/342

(58) Field of Classification Search ........ 356/445–448; 250/216, 227.14, 227.24, 227.25; 156/338, 156/342
See application file for complete search history.

(56) References Cited

U.S. PATENT DOCUMENTS

| 4,844,613 A | * | 7/1989 | Batchelder et al. ......... 356/318 |
| 6,415,235 B1 | | 7/2002 | Bartholomew et al. |
| 6,577,396 B1 | | 6/2003 | Naya |
| 6,654,123 B1 | * | 11/2003 | Shimizu ..................... 356/445 |
| 2002/0040426 A1 | | 4/2002 | Kamitani et al. |
| 2002/0046992 A1 | | 4/2002 | Inaki et al. |
| 2002/0093659 A1 | * | 7/2002 | Shimizu ..................... 356/445 |

FOREIGN PATENT DOCUMENTS

| EP | 1 219 953 A1 | 7/2002 |
| JP | 6-167443 A | 6/1994 |
| JP | 2001-330560 A | 11/2001 |
| WO | WO 01/84120 A2 | 11/2001 |

OTHER PUBLICATIONS

S. Jolander et al., "Integrated Fluid Handling System for Biomolecular Interaction Analysis", Analytical Chemistry, American Chemical Society. Columbus, US, vol. 63, No. 20, Oct. 15, 1991, pp. 2338-2345, XP000275479.

(Continued)

*Primary Examiner*—Thomas H. Tarcza
*Assistant Examiner*—Isam Alsomiri
(74) *Attorney, Agent, or Firm*—Sughrue Mion, PLLC

(57) ABSTRACT

A measuring apparatus comprising a measuring chip, an optical incidence system, a photodiode array, a differentiation part, and a computation part. The differentiation part differentiates an optical detection signal output from each light-receiving element, in a direction where light-receiving elements are juxtaposed, at intervals of outputs of two adjacent light-receiving elements. The computation part specifies a reference light-receiving element, then judges whether or not values of the optical detection signals of a first predetermined number of light-receiving elements increase monotonously in directions going to both sides, and computes a position of a dark line on the basis of a value obtained by differentiating the outputs of a second predetermined number of light-receiving elements sandwiching the reference light-receiving element when it is judged that the values of the optical detection signals increase monotonously, in the above-described direction.

23 Claims, 8 Drawing Sheets

OTHER PUBLICATIONS

European Search Report for 05009698.1-2204 PCT/ dated Aug. 16, 2005.

Timmer J et al: "Numerical methods to determine calcium release flux from calcium transients in muscle cells" Biophysical Journal, vol. 74, No. 4, Apr. 1998, pp. 1694-1707, XP002337149, ISSN: 0006-3495, *p. 1696, right-hand column, paragraph 2- p. 1697, left-hand column, paragraph 3*.

* cited by examiner

| TIME | Dfch | Df_Val | α | l |
|---|---|---|---|---|
| Pre | r | Vr | αr | 0 |
| 0 | m₀ | Vm₀ | αm₀ | l₀ |
| 1 | m₁ | Vm₁ | αm₁ | l₁ |
| 2 | m₂ | Vm₂ | αm₂ | l₂ |
| 3 | m₃ | Vm₃ | αm₃ | l₃ |
| ⋮ | ⋮ | ⋮ | ⋮ | ⋮ |

SURFACE PLASMON RESONANCE MEASURING APPARATUS

BACKGROUND OF THE INVENTION

1. Field of the Invention

The present invention relates to a measuring apparatus, utilizing an evanescent wave, which analyzes a sample by causing a light beam to reflect at the interface between a thin film layer in contact with the sample and a dielectric block portion to generate an evanescent wave and then measuring a change in the intensity of the totally reflected light beam due to the evanescent wave.

2. Description of the Related Art

If free electrons vibrate collectively in a metal, a compression wave called a plasma wave will be generated. The compression wave, generated in the metal surface and quantized, is called a surface plasmon.

There are various kinds of surface plasmon resonance measuring apparatuses for quantitatively analyzing a substance in a liquid sample by taking advantage of a phenomenon that the surface plasmon is excited by a light wave. Among such apparatuses, one employing the "Kretschmann configuration" is particularly well known (e.g., see Japanese Unexamined Patent Publication No. 6(1994)-167443).

The surface plasmon resonance measuring apparatus employing the aforementioned "Kretschmann configuration" is constructed basically of (1) a dielectric block portion formed into the shape of a prism; (2) a metal film, formed on one surface of the dielectric block portion, for placing a measurement substance (which is a substance to measured) such as a liquid sample thereon; (3) a light source for emitting a light beam; (4) an optical system for making the light beam enter the dielectric block portion at various angles of incidence so that a condition for total internal reflection is satisfied at the interface between the dielectric block portion and the metal film; and (5) photodetection means for detecting the state of surface plasmon resonance (SPR), that is, state of attenuated total reflection (ATR) by measuring the intensity of the light beam totally reflected at the interface; and (6) measurement means for measuring the state of surface plasmon resonance (SPR) on the basis of the result of detection obtained by the photodetection means.

In order to obtain various angles of incidence in the aforementioned manner, a relatively thin light beam may be caused to strike the above-described interface at various incidence angles, or a relatively thick light beam may be caused to strike the interface convergently or divergently so that it has incident components at various angles. In the former, a light beam whose reflection angle varies with a change in the incidence angle can be detected by a small photodetector movable in synchronization with a change in the reflection angle, or by an area sensor extending in the direction where the reflection angle varies. In the latter, on the other hand, light beams reflected at various angles can be detected by an area sensor extending in a direction where the reflected light beams can be all received.

In the above-described surface plasmon resonance measuring apparatus, if a light beam strikes a metal film at a specific incidence angle $\theta_{sp}$ greater than a critical incidence angle at which total internal reflection (TIR) takes place, an evanescent wave having electric field distribution is generated in a measurement substance (liquid sample to be measured) in contact with the metal film. This evanescent wave excites the above-described surface plasmon in the interface between the metal film and the measurement substance (liquid sample to be measured). When the wave number vector of the evanescent wave is equal to the wave number of the surface plasmon and therefore the wave numbers between the two are matched, the evanescent wave resonates with the surface plasmon and the light energy is transferred to the surface plasmon. As a result, the intensity of the light totally reflected at the interface between the dielectric block portion and the metal film drops sharply. This sharp intensity drop is generally detected as a dark line by the above-described photodetection means.

Note that the aforementioned resonance occurs only when an incident light beam is p-polarized light. Therefore, it is necessary to make settings in advance so that an incident light beam strikes the aforementioned interface as p-polarized light.

If the wave number of the surface plasmon is found from an incidence angle $\theta_{sp}$ at which attenuated total reflection (ATR) takes place (the incidence angle $\theta_{sp}$ will hereinafter be referred to as a total reflection attenuation angle $\theta_{sp}$), the dielectric constant of a measurement substance (liquid sample) can be calculated by the following Equation:

$$K_{sp}(\omega) = \frac{\omega}{c}\sqrt{\frac{\varepsilon_m(\omega)\varepsilon_s}{\varepsilon_m(\omega)+\varepsilon_s}}$$

where $K_{sp}$ represents the wave number of the surface plasmon, $\omega$ represents the angular frequency of the surface plasmon, c represents the speed of light in vacuum, and $\varepsilon_m$ and $\varepsilon_s$ represent the dielectric constants of the metal and the measurement substance, respectively.

That is, the properties related to the refractive index, can be found by finding the total reflection attenuation angle $\theta_{sp}$ which is an incidence angle at which the intensity of reflected light reduces In this kind of surface plasmon resonance measuring apparatus, a photodiode array (photodetection means) can be employed with the object of measuring the aforementioned total reflection attenuation angle $\theta_{sp}$ accurately in a large dynamic range, as disclosed in U.S. Pat. No. 6,577,396. The photodetection means is constructed of a plurality of light-receiving elements juxtaposed in a predetermined direction. The light-receiving elements are juxtaposed to respectively receive the components of a light beam totally reflected at the aforementioned interface at various reflection angles.

In that case, there is provided differentiation means to differentiate optical detection signals output by the light-receiving elements of the aforementioned photodetection means, in the direction where the light-receiving elements are juxtaposed. Based on differentiated values output by this differentiation means, the total reflection attenuation angle $\theta_{sp}$ is specified, whereby the properties related to the refractive index of a measurement substance are often analyzed.

In addition, a leaky mode measuring apparatus is known as a similar measuring apparatus making use of an evanescent wave (for example, see "Spectral Researches," Vol. 47, No. 1 (1998), pp. 21 to 23 and pp. 26 to 27). This leaky mode measuring apparatus consists basically of (1) a dielectric block portion formed into the shape of a prism; (2) a cladding layer formed on one surface of the dielectric block portion; (3) an optical waveguide layer, formed on the cladding layer, for placing a liquid sample thereon; (4) a light source for emitting a light beam; (5) an optical system for making the light beam enter the dielectric block portion at various angles of incidence so that a condition for total internal reflection is satisfied at the interface between the dielectric block portion and the cladding layer; and (6) photodetection means for detecting the excited state of a waveguide mode, that is, state of attenuated total reflection (ATR) by measuring the intensity of the light beam totally reflected at the above-described interface.

In the above-described leaky mode measuring apparatus, if a light beam strikes the cladding layer through the dielectric block portion at an incidence angle greater than a critical incidence angle at which total internal reflection (TIR) takes place, the light beam is transmitted through the cladding layer. Thereafter, in the optical waveguide layer formed on the cladding layer, only light with a specific wave number, incident at a specific incidence angle, propagates in a waveguide mode. If the waveguide mode is excited in this manner, most of the incident light is confined within the optical waveguide layer, and consequently, attenuated total reflection (ATR) occurs in which the intensity of light totally reflected at the aforementioned interface drops sharply. And the wave number of the light propagating through the optical waveguide layer depends upon the refractive index of the measurement substance (liquid sample) on the optical waveguide layer. Therefore, by finding the total reflection attenuation angle $\theta_{sp}$ at which attenuated total reflection ATR occurs, the refractive index of the measurement substance and the properties of the measurement substance related to the refractive index can be analyzed.

Note that the leaky mode measuring apparatus can also employ the aforementioned photodetection means (photodiode array) to detect the position of a dark line that occurs in reflected light because of attenuated total reflection (ATR) Also, in many cases, in addition to the photodetection means, the aforementioned differentiation means is employed in the leaky mode measuring apparatus.

In the field of pharmaceutical research, the above-described surface plasmon resonance measuring apparatus and leaky mode measuring apparatus are sometimes used in a random screening method for detecting a specific substance that couples to a sensing substance that is desired. In this case, a sensing substance is fixed as the above-described measurement substance on the aforementioned thin film layer (which is the aforementioned metal film in the case of surface plasmon resonance measuring apparatuses, or the cladding layer and optical waveguide layer in the case of leaky mode measuring apparatuses). Then, a liquid sample containing various inspection substances (which are substances to be inspected) is added to the sensing substance. And each time a predetermined time elapses, the total reflection attenuation angle $\theta_{sp}$ is measured.

If an inspection substance in the liquid sample is a substance that couple to the sensing substance, then the coupling will cause the refractive index of the sensing substance to vary with the lapse of time. Therefore, every time a predetermined time elapses, the total reflection attenuation angle $\theta_{sp}$ is measured. Based on the measured value, it is measured whether or not a change has occurred in the total reflection attenuation angle $\theta_{sp}$. Based on this result, it can be judged whether or not the inspection substance is a specific substance that couples with the sensing substance. Examples of such a combination of a specific substance and a sensing substance are a combination of an antigen and an antibody, and a combination of an antibody and an antibody. More specifically, a rabbit anti-human IgG antibody and a human IgG (immunoglobulin G) antibody can be used as a sensing substance (which is fixed on a thin film layer) and a specific substance, respectively.

Note that in order to measure the coupled state between an inspection substance in a liquid sample and a sensing substance, the total reflection attenuation angle $\theta_{sp}$ itself does not always need to be detected. For example, a liquid sample with a target substance is added to a sensing substance. Next, a change in the total reflection attenuation angle $\theta_{sp}$ is measured. Based on the magnitude of the change, the coupled state between the inspection substance and the sensing substance can be measured. In the case where the aforementioned photodetection means and differentiation means are employed in a measuring apparatus utilizing ATR, a quantity of change in a differentiated value corresponds to a quantity of change in the total reflection attenuation angle $\theta_{sp}$. Therefore, based on a quantity of change in a differentiated value, the coupled state between the sensing substance and the target substance can be measured (see Japanese Unexamined Patent Publication No. 2003-172694).

In the above-described measuring method and apparatus that utilize ATR, a liquid sample consisting of a solvent and an inspection substance is supplied to a cup-shaped or Petri dish-shaped measuring chip in which a sensing substance is fixed on a thin film layer formed on the bottom surface, and the above-described quantity of change in the total reflection attenuation angle $\theta_{sp}$ is measured.

Note that in Japanese Unexamined Patent Publication No. 2001-330560, there is disclosed a measuring apparatus, utilizing ATR, which is capable of measuring a great number of samples in a short time by serially measuring a plurality of measuring chips mounted in a turntable, etc.

In U.S. Patent Laid-Open No 20020046992, there is also disclosed a measuring apparatus, utilizing ATR, which performs measurements, employing a measuring chip provided with a plurality of sample-holding portions. In such a measuring apparatus, a great number of samples can be measured in a short time without moving the measuring chip.

In the above-described conventional measuring apparatuses, incidentally, a difference between adjacent light-receiving elements in the above-described photodetection means is generally computed by differentiation means and is output as a differentiated value. However, there are cases where there is an individual difference between the sensitivities of the light-receiving elements or cases where signals from the light-receiving elements undergo various noise or waveform distortion. In such a case, for example, a differentiated value, which should decrease and increase before and after a dark line according to an increase in an incidence angle $\theta$, increases and then decreases. That is, a differentiated value does not vary linearly with a change in the incidence angle $\theta$, and consequently, there is a possibility that accuracy in measuring the state of attenuated total reflection (ART) will degrade.

SUMMARY OF THE INVENTION

The present invention has been made in view of the above-described circumstances. Accordingly, it is the object of the present invention to provide a measuring apparatus that is capable of measuring the state of attenuated total reflection (ART) accurately, even when there is an individual difference between the sensitivities of light-receiving elements, and even when signals from light-receiving elements contain various noise or waveform distortions.

To achieve this end and in accordance with the present invention, there is provided a first measuring apparatus comprising:

a measuring chip comprising
a dielectric block portion, a thin film layer formed on one surface of the dielectric block portion, and a sample holding mechanism for holding a sample on a surface of the thin film layer;

a light source for emitting a light beam;

an optical incidence system for causing the light beam to enter the dielectric block portion at angles of incidence so that a total internal reflection condition is satisfied at an interface between the dielectric block portion and the thin film layer;

photodetection means, which comprises a plurality of light-receiving elements, for detecting intensities of the light beam whose incidence angles are different, totally reflected at the interface;

differentiation means for differentiating an optical detection signal output from each of the light-receiving elements of the photodetection means, in a direction where the light-receiving elements are juxtaposed, at intervals of outputs of two adjacent light-receiving elements; and computation means for specifying a reference light-receiving element by a predetermined method, then judging whether or not values of the optical detection signals of a first predetermined number of light-receiving elements increase monotonously in directions going to both sides with the reference light-receiving element as center, and computing a position of a dark line, contained in the light beam reflected at the interface, on the basis of a value obtained by differentiating the outputs of a second predetermined number of light-receiving elements sandwiching the reference light-receiving element when it is judged that the values of the optical detection signals increase monotonously, in the direction where the light-receiving elements are juxtaposed.

In the first measuring apparatus of the present invention, the predetermined method specifies a light-receiving element, which outputs an optical detection signal having a minimum value, among the light-receiving elements, as the aforementioned reference light-receiving element.

In the first measuring apparatus of the present invention, when the outputs of two adjacent light-receiving elements are differentiated in the direction where the light-receiving elements are juxtaposed, the predetermined method may specify two light-receiving elements whose differentiated value is nearest to 0, as reference light-receiving elements. In this case, while two light-receiving elements are specified as reference light-receiving elements, the above-described judgement may be performed on only one of the two, or the above-described judgement may be performed on both light-receiving elements.

In the aforementioned measuring apparatus, there are cases where the waveform in a beam profile of optical detection signals detected by the light-receiving elements, in addition to a valley due to a dark line produced by the above-described surface plasmon resonance effect, etc., has a valley formed by superposition of noise such as spike noise, etc. If the beam profile has a plurality of valleys, a plurality of zero-crossing points will occur in a differentiated signal and it will become difficult to compute the position of a dark line accurately.

The waveform of the valley due to noise generally forms a sharp valley with a narrow width, whereas the waveform of the valley formed by a dark line has a certain degree of width according to the optical system of the measuring apparatus. Hence, in the present invention, the aforementioned method specifies a reference light-receiving element from the beam profile detected by the photodetection means. Next, it is judged whether or not values of the optical detection signals of a first predetermined number of light-receiving elements increase monotonously in directions going to both sides with the reference light-receiving element as center. Next, values are obtained by differentiating the outputs of a second predetermined number of light-receiving elements sandwiching the reference light-receiving element when it is judged that the values of the optical detection signals increase monotonously, in the direction where the light-receiving elements are juxtaposed. Based on the differentiated values, that is, based on differentiated signals, an area corresponding to a dark line is specified. And based on the position of a zero-crossing point, the position of a dark line is measured. This renders it possible to compute the position of a dark line accurately.

Note that the first predetermined number in the expression "first predetermined number of light-receiving elements" does not need to be the same as the second predetermined number in the expression "second predetermined number of light-receiving elements sandwiching the reference light-receiving element." They may be different numbers.

In accordance with the present invention, there is provided a second measuring apparatus comprising:

a measuring chip comprising
 a dielectric block portion,
 a thin film layer formed on one surface of the dielectric block portion, and
 a sample holding mechanism for holding a sample on a surface of the thin film layer;

a light source for emitting a light beam;

an optical incidence system for causing the light beam to enter the dielectric block portion at angles of incidence so that a total internal reflection condition is satisfied at an interface between the dielectric block portion and the thin film layer;

photodetection means, which comprises a plurality of light-receiving elements, for detecting intensities of the light beam whose incidence angles are different, totally reflected at the interface;

differentiation means for differentiating an optical detection signal output from each of the light-receiving elements of the photodetection means, in a direction where the light-receiving elements are juxtaposed, at intervals of outputs of two adjacent light-receiving elements; and computation means for computing a position of a dark line that is obtained in actual measurement by computing a distance (L) from a predetermined baseline to the position of the dark line, using the following equation:

$$L = (m-r) \times R - Vr/\alpha r + Vm/\alpha m$$

in which R is a dynamic range per one differential channel when one difference channel comprises two adjacent light-receiving elements, r is the order of arrangement of a differential channel corresponding to the predetermined baseline, Vr is a voltage value equivalent to a differentiated value that represents the baseline output by the $r^{th}$ differential channel, $\alpha r$ is the differential gradient of the $r^{th}$ differential channel, m is the order of arrangement of a differential channel that detected the dark line contained in the light beam reflected at the interface, Vm is a voltage value equivalent to a differentiated value output by the $m^{th}$ differential channel, and am is the differential gradient of the $m^{th}$ differential channel.

The dynamic range R refers to a width of detection per one differential channel, that is, the pitch between the above-described light-receiving elements juxtaposed. Also, the differential gradient means a gradient obtained by dividing the dynamic range of voltages of differential channels by the pitch between the above-described light-receiving elements.

In the aforementioned measuring apparatus, in the case where there is an individual difference between the sensitivity characteristics of the light-receiving elements of a photodiode array, an error will occur in the width of detection that two adjacent light-receiving elements have, and consequently, the output characteristic of the photodetection means with respect to the position of a dark line will become non-linear. Therefore, in a conventional method (in which, between a light-receiving element corresponding to a specific baseline and a light-receiving element detecting a dark line, the detection widths for element groups consisting of two adjacent light-receiving elements are added and a distance from the baseline to the dark line position is computed), there is a possibility that the dark line position cannot be accurately computed.

Hence, in the present invention, a baseline is previously set, and the number of differential channels from a differential channel corresponding to the baseline to a differential channel detecting a dark line is multiplied by the dynamic range (width of detection per one differential channel), whereby a distance from the baseline to the dark line position is computed. This renders it possible to compute the position of a dark line accurately without being influenced by the individual difference between the sensitivity characteristics of the light-receiving elements of a photodiode array.

In accordance with the present invention, there is provided a third measuring apparatus comprising:
  a measuring chip comprising
    a dielectric block portion,
    a thin film layer formed on one surface of the dielectric block portion, and
    a sample holding mechanism for holding a sample on a surface of the thin film layer;
  a light source for emitting a light beam;
  an optical incidence system for causing the light beam to enter the dielectric block portion at angles of incidence so that a total internal reflection condition is satisfied at an interface between the dielectric block portion and the thin film layer;
  photodetection means, which comprises a plurality of light-receiving elements, for detecting intensities of the light beam whose incidence angles are different, totally reflected at the interface;
  difference means for computing optical detection signals based on outputs of the light-receiving elements and computing a difference between the optical detection signals with the space of at least one light-receiving element in a direction where the light-receiving elements are juxtaposed; and
  computation means for measuring a state of attenuated total reflection, based on the difference computed by the difference means.

In the third measuring apparatus of the present invention, the aforementioned optical detection signal may be an average value obtained by dividing a plurality of light-receiving elements into light-receiving element groups containing a predetermined number of light-receiving elements which are at least two adjacent light-receiving elements, and then averaging the outputs of the light-receiving elements of each of the light-receiving element groups. Note that the aforementioned average value is not limited to an average value itself, but it may be a value equivalent to an average value. For instance, it may be a total value of the outputs of the light-receiving elements, a value obtained by dividing a total value by a desired value, a value obtained by multiplying a total value by a desired value, etc.

In the third measuring apparatus of the present invention, the aforementioned optical detection signal may be an average value obtained by serially computing an average value of at least two adjacent light-receiving elements in the direction where the light-receiving elements are juxtaposed. Note that the average value of adjacent light-receiving elements is not limited to an average value itself, but it may be a value equivalent to an average value. For example, it may be a total value of the outputs of the light-receiving elements, a value obtained by dividing a total value by a desired value, a value obtained by multiplying a total value by a desired value, etc.

In the third measuring apparatus of the present invention, the aforementioned computation means may measure the state of attenuated total reflection by measuring the state of the dark line contained in the light beam. The pitch between the light-receiving elements may be one-fourth or less of the half-value width of the dark line. The half-value width of the dark line is intended to mean the width of a dark line as the light quantity of the dark line is reduced to ½ of the maximum attenuation value.

The third measuring apparatus of the present invention may further comprise sensitivity correction means that corrects for a difference in sensitivity between the light-receiving elements of the photodetection means.

The aforementioned sensitivity correction means may correct for a difference in sensitivity between the light-receiving elements of the photodetection means by processing signals.

The above-described three measuring apparatuses are the aforementioned surface plasmon resonance apparatus that employs a metal film as the above-described thin film layer; the aforementioned leaky mode measuring apparatus that employs a layer, consisting of a cladding layer formed on one surface of a dielectric block portion and an optical waveguide layer formed on the cladding layer, as the above-described thin film layer; and so on.

In the measurement apparatus of the present invention, there are various methods of analyzing a sample by detecting the intensity of a light beam totally reflected at the aforementioned interface with photodetection means. For example, a light beam is caused to strike the aforementioned interface at various angles of incidence so that a total internal reflection condition is satisfied at the interface. Then, the intensity of the light beam totally reflected at the interface is measured at each position corresponding to each incidence angle. Next, by detecting the position (angle) of a dark line generated due to attenuated total reflection (ATR), a sample held by the measuring chip is analyzed. In addition, a light beam with a plurality of wavelengths is caused to enter a measuring chip at angles of incidence so that a total internal reflection condition is satisfied at the interface. Then, the intensity of the light beam totally reflected at the interface is measured for each wavelength. Next, by measuring the degree of ATR (position and degree of a dark line) for each wavelength, a sample held by the measuring chip is analyzed (see D. V. Noort, K. Johansen, C. -F. Mandenius, Porous Gold in Surface Plasmon Resonance Measurement, EUROSENSORS XIII, 1999, pp. 585–588).

In the first measuring apparatus according to the present invention, the intensities of a light beam are measured by a plurality of light-receiving elements, and the position of a dark line is detected by differentiating the optical detection signals of the light-receiving elements at intervals of the outputs of two adjacent light-receiving elements. The computation means of the first measuring apparatus specifies a reference light-receiving element by a predetermined method, then judges whether or not values of the optical detection signals of a first predetermined number of light-receiving elements increase monotonously in directions going to both sides with the reference light-receiving element as center, and computes the position of a dark line on the basis of a value obtained by differentiating the outputs of a second predetermined number of light-receiving elements sandwiching the reference light-receiving element (i.e., the light-receiving element that detects a valley of a dark line area having a certain degree of width) when it is judged that the values of the optical detection signals increase monotonously, in the direction where the light-receiving elements are juxtaposed. Therefore, even in the case where there are a plurality of zero-crossing points in a differentiated signal because of the occurrence of spike noise, etc., it is possible to compute the position of a dark line accurately.

In addition, in the second measuring apparatus according to the present invention, a baseline is previously set, and the number of differential channels from a differential channel corresponding to the baseline to a differential channel detecting a dark line is multiplied by the dynamic range (width of detection per one differential channel), whereby a distance from the baseline to the position of the dark line is computed. Therefore, it becomes possible to compute the position of a dark line accurately without being influenced by the individual difference between the sensitivity characteristics of the light-receiving elements of a photodiode array.

Further, the third measuring apparatus according to the present invention is equipped with photodetection means, which comprises a plurality of light-receiving elements, for detecting intensities of the light beam totally reflected at the interface between the dielectric block portion and the thin film layer; and difference means for computing optical detection signals based on outputs of the light-receiving elements and computing a difference (described as a skip difference value) between the optical detection signals with the space of at least one light-receiving element in a direction where the light-receiving elements are juxtaposed. Based on the skip difference value, the state of attenuated total reflection is measured. The skip difference value is unsusceptible to noise, so a change in the skip difference value is enhanced in linearity compared to a change in a difference value that is used in prior art, and the state of attenuated total reflection can be accurately measured. In addition, the skip difference value has a greater value than a difference value, so sensitivity in measuring the state of attenuated total reflection is enhanced.

BRIEF DESCRIPTION OF THE DRAWINGS

The present invention will be described in further detail with reference to the accompanying drawings wherein.

DESCRIPTION OF THE PREFERRED EMBODIMENTS

Figure 1:
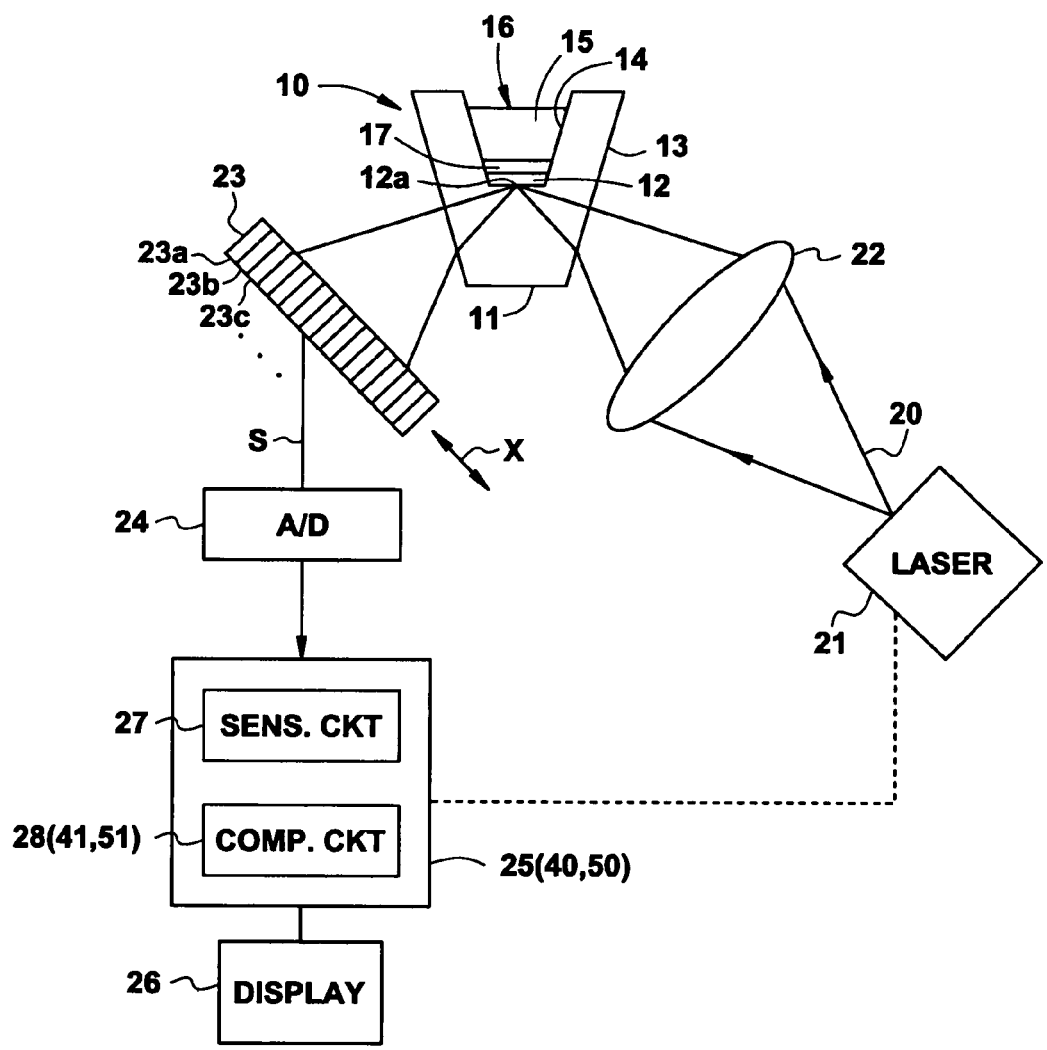
FIG. 1 is a side view showing a surface plasmon resonance measuring apparatus constructed in accordance with a first embodiment of the present invention.

Referring now to FIG. 1, there is shown a surface plasmon resonance measuring apparatus constructed in accordance with a first embodiment of the present invention. The surface plasmon resonance measuring apparatus shown in the figure includes a disposable measuring chip 10; a laser light source 21, such as a semiconductor laser, etc., which emits a measuring light beam (laser beam) 20; a condenser lens 22 that is an optical incidence system; a photodiode array 23; an A/D converter 24 that converts the output signal of the photodiode array 23 into a digital signal; a signal processing unit 25 that performs processing to be described later in response to the digitized output signal; and a display unit 26.

The measuring chip 10 consists of a lower dielectric block portion 11, a first thin film layer 12, an upper sample holding portion 13, and a second thin film layer 14. The lower dielectric block portion 11 is formed into the shape of a truncated quadrangular pyramid. The first thin film layer 12 is formed on the top surface of the lower dielectric block portion 11 and made of gold, silver, copper, aluminum, etc. The upper sample holding portion 13 is formed on the lower dielectric block portion 11 and consists of a cylindrical portion that forms a liquid sample space on the first thin film layer 12 to hold a liquid sample 15. The second thin film layer 12 is formed on the tapered interior wall surface of the upper sample holding portion 13 which increases in diameter from its lower end (the first thin film layer 12) to its upper end. The tapered space within the upper sample holding portion 13 serves as a well portion 16 for holding the liquid sample 15.

The lower dielectric block portion 11 and upper sample holding portion 13, which constitute the measuring chip 10, are integrally formed, for example, from a transparent resin, etc. The first thin film layer 12 and second thin film layer 14 are formed by vapor deposition. In the first embodiment shown in FIG. 1, a sensing substance 17 is fixed on the first thin film layer 12 and second thin film layer 14, and the liquid sample 15 contains various kinds of proteins.

The condenser lens 22 collects the light beam 20 emitted from the light source 21, and causes the collected light beam 20 to converges at the interface 11a between the lower dielectric block portion 11 and the first thin film layer 12a so that various angles of incidence are obtained. The range of incidence angles is set so that a total internal reflection (TIR) condition for the light beam 20 is satisfied at the interface 12a, and also surface plasmon resonance (SPR) can take place.

Note that the light beam 20 strikes the interface 12b as p-polarized light. To do so, the laser light source 21 needs to be arranged so that the polarization direction of the light beam 20 becomes a predetermined direction. Alternatively, the polarization direction of the light beam 20 may be controlled with a wavelength plate, a polarizing plate, etc. The photodiode array 23 consists of a great number of photodiodes 23a, 23b, 23c, . . . , which are juxtaposed in the direction of arrow X shown in FIG. 1. The output signal of the photodiode array 23 is constructed of signals Sa, Sb, Sc, . . . , output from the photodiodes 23a, 23b, 23c, . . . .

The signal processing unit 25 controls operation of each part and has a sensitivity correction part 27 and a computation part 28. The sensitivity correction part 27 corrects for the sensitivities of the digitized output signals Sa, Sb, Sc, . . . of the photodiode array 23. The computation part 28 computes a skip difference value F and finds a total reflection attenuation angle θsp, based on the skip difference value F.

Now, a description will be given of how a liquid sample is analyzed by the above-described surface plasmon resonance measuring apparatus. Initially, to acquire a correction value that corrects for a difference in sensitivity between the photodiodes 23a, 23b, 23c, . . . of the photodiode array 23 prior to measurement, a light beam emitted from a standard light source is caused to strike the interface 12a so that light intensities with respect to the photodiode array 23 become uniform. Note that the standard light source can use a direct current light source from which uniform light intensity distribution is obtained.

The signals Sa, Sb, Sc, . . . output from the photodiodes 23a, 23b, 23c, . . . of the photodiode 23 are converted into digital signals by the A/D converter 24 and are input to the sensitivity correction part 27 of the signal processing unit 25. The sensitivity correction part 27 computes an average value $S_{av}$ of the output signals Sa, Sb, Sc, . . . and then computes sensitivity correction coefficients $S_{av}$/Sa, $S_{av}$/Sb, $S_{av}$/Sc, . . . and stores the coefficients so that they correspond to the output signals. The signals Sa, Sb, Sc, . . . input to the sensitivity correction part 27 are multiplied by the corresponding sensitivity correction coefficients, and the corrected signals Sa', Sb', Sc', . . . are input to the computation part 28. Note that the operation of setting sensitivity correction coefficients does not need to be performed for each measurement. The setting operation may be performed as occasion demands.

After the setting of the sensitivity correction coefficients, actual measurement is performed. The measuring chip 10 is supplied with the liquid sample 15. In response to a command from the signal processing unit 25, the laser light source 21 is driven, and as described above, the light beam 20 is emitted so that it converges at the interface 12a between the dielectric block portion 11 and the first thin film layer 12. The light beam 20 totally reflected at the interface 12a is detected by the photodiode array 23.

The signals Sa, Sb, Sc, . . . output from the photodiodes 23a, 23b, 23c, . . . of the photodiode 23 are converted into digital signals by the A/D converter 24 and are input to the sensitivity correction part 27, in which a correction process is performed. The corrected signals Sa', Sb', Sc', . . . are output to the computation part 28.

The computation part 28 serially computes a skip difference value F that is a difference between the outputs of alternate photodiodes. More specifically, it serially computes (Sc'−Sa'), (Sd'−Sb'), (Se'−Sc') . . . .

FIG. 2 illustrates the relationship between the incidence angle θ of the light beam 20 totally reflected at the interface 12a and the skip difference value F. Now, assume that the relationship between the incidence angle θ of the light beam 20 at the interface 12a and the light intensity I of the reflected light beam incident on the photodiodes 23a, 23b, 23c . . . is as shown in FIG. 2A.

Figure 2A:
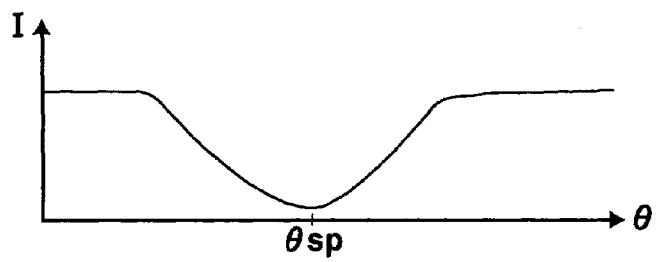
FIG. 2A is a graph showing the relationship between the incidence angle θ of a light beam at an interface and the light intensity I of the light beam reflected at that interface.

The light beam 20 incident at a certain specific incidence angle θsp on the interface 12a excites a surface plasmon in the interface between the first thin film layer 12 and the sensing substance 17, so the light intensity I of the light beam 20 reflected at that interface drops sharply as shown in FIG. 2A. This specific incidence angle θsp is referred to as a total reflection attenuation angle θsp. The light intensity of the light beam reflected at the total reflection attenuation angle θsp has a minimum value. And a reduction in the light intensity I is observed as a dark line in the reflected light.

Figure 2B:
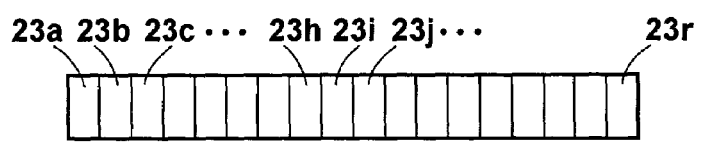
FIG. 2B is a diagram showing how the photodiodes shown in FIG. 2A are arranged.
Figure 2C:
FIG. 2C is a graph showing the relationship between the positions of the photodiodes (i.e., incidence angles θ of the light beam) and the output signals of the photodiodes.
Figure 2D:
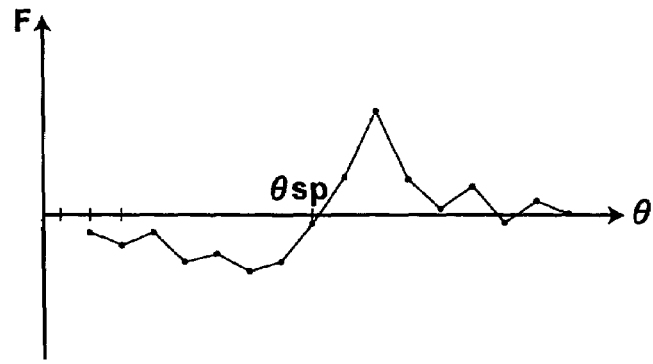
FIG. 2D is a graph showing the relationship between the incidence angle θ and the skip difference value F between the outputs of alternate photodiodes.

FIG. 2B illustrates how the photodiodes 23a, 23b, 23c . . . are arranged. The positions of the photodiodes 23a, 23b, 23c . . . correspond to the above-described various incidence angles, respectively. FIG. 2C illustrates the relationship between the positions of the photodiodes 23a, 23b, 23c . . . (i.e., incidence angles θ of the light beam 20) and the output signals (sensitivity-corrected signals) Sa', Sb', Sc' . . . of the photodiodes 23a, 23b, 23c . . . . The pitch between the photodiodes 23a, 23b, 23c . . . is narrow and one-fourth or less of the half-value width of a dark line shown in FIG. 2A. Because of this, the signal values output from the photodiodes 23a, 23b, 23c, . . . are small and susceptible to noise, so a graph shown in FIG. 2C is not satisfactory in linearity. And the relationship between the incidence angle θ and the skip difference value F is as shown in FIG. 2D.

The computation part 28 computes the skip difference values F and then computes the total reflection attenuation angle θsp from the photodiode that has an output near to difference value F=0 corresponding to the total reflection attenuation angle θsp, based on the computed skip difference values F.

Figure 3:
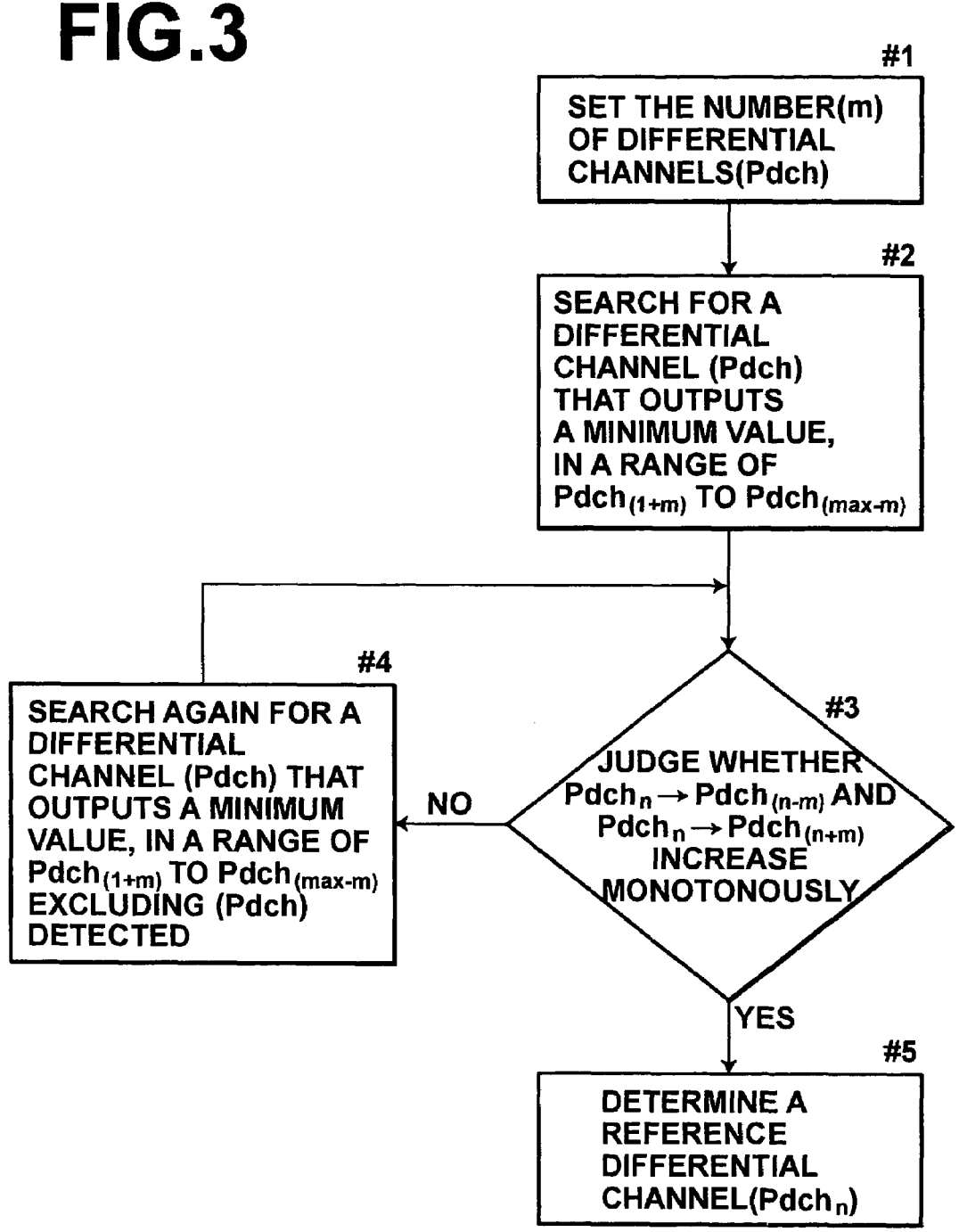
FIG. 3 is a flowchart showing how a reference light-receiving element is detected.

Now, a description will be given of how a dark line (total reflection attenuation angle θsp) is computed by the computation part 28. The process of computing a dark line is shown in FIG. 3. In the figure, processing steps are represented by symbols marked with #.

Before explaining the processing steps, symbols used herein are defined as follows. The channel of each photodiode is represented as "Pdch." A signal, output from each photodiode (Pdch) and corrected by the sensitivity correction part 27, is represented as "Pd_val." A differential amplifier to which alternate photodiodes ($Pdch_n$ and $Pdch_{n+2}$) are connected, that is, a differential (skip differential) channel is represented as "Dfch." The output voltage value ($Pd\_val_{n+1} - Pd\_val_n$) of the signal of a differential channel (Dfch) is represented as "Df_val."

Initially, the number (m) of channels (Pdch) for judging a dark line is set (step #1). The width of a dark line varies with the arrangement of an optical system in a measuring apparatus. Therefore, based on the width of a dark line that occurs in a measuring apparatus, the number (m) of channels (Pdch) is set to a value capable of suitably detecting a dark line. In the first embodiment, the number (m) is set to 3.

Next, as a reference light-receiving element, a search for $Pdch_n$ in which Pd_val detected a minimum value is made in a range of $Pdch_{(1+m)}$ to $Pdch_{(max-m)}$ (step #2). The photodiode array 23 in the first embodiment is constructed of 18 channels (photodiodes 23a to 23r) and the number (3) is 3, so the above-described range includes photodiodes 23d to 23o, and in this range, $Pdch_n$ detecting a minimum value is a photodiode 23i.

Next, it is judged whether or not the detected signal values of the light-receiving elements in the range of the number (m) are increasing monotonously in directions going to both sides with the acquired $Pdch_n$ as reference, that is, it is judged whether or not $Pdch_n$->$Pdch_{(n-m)}$ and $Pdch_n$->$Pdch_{(n+m)}$ are increasing monotonously (step #3). When they are increasing monotonously, the $Pdch_n$ is set as a reference light-receiving element (step #5). On the other hand, when they are not increasing monotonously, a search for $Pdch_n$ having a minimum value is made excluding the detected Pdch (step #4), and step #3 is repeated. In the first embodiment, the detected signal values of three channels are increasing monotonously in directions going to both sides, with photodiode 23i as reference. Therefore, the photodiode 23i is set as a reference light-receiving element.

And a differential channel (Dfch), which has an output nearest to skip difference value F (Df_val)=0, among a predetermined number of photodiodes (which does not always need to correspond to the number (m)) sandwiching the specified photodiode ($Phch_n$), is selected, and based on the skip difference value F, the total reflection attenuation angle θsp is computed.

According to the first embodiment, as described above, it is judged whether or not the detected signal values of a predetermined number of light-receiving elements increase monotonously in directions going to both sides with a reference photodiode (specified from a beam profile by a predetermined method) as center. And when the detected signal values increase monotonously, a reference light-receiving element, that is, a dark line region with a certain degree of width is specified, whereby noise is prevented from being taken for a dark line.

In addition, the skip difference value, which is a difference between the outputs of alternate photodiodes in the direction where the photodiodes are arranged, is serially computed, and based on the skip difference value, the total reflection attenuation angle θsp is computed. The skip difference value is unsusceptible to noise, so a change in the skip difference value is enhanced in linearity compared to a change in a difference value that is used in prior art, and the total reflection attenuation angle θsp can be measured with a high degree of accuracy. In addition, the skip difference value has a greater value than a difference value, so sensitivity in measuring the state of attenuated total reflection is enhanced.

Furthermore, in the sensitivity correction part 27, the signals Sa, Sb, Sc . . . output from the photodiodes 23a, 23b, 23c . . . are multiplied by the corresponding sensitivity correction coefficients $S_{av}$/Sa, $S_{av}$/Sb, $S_{av}$/Sc . . . , and the corrected signals Sa', Sb', Sc' . . . , in which a correction for a difference in sensitivity between the photodiodes has been made, are obtained. And based on the corrected signals Sa', Sb', Sc' . . . , the total reflection attenuation angle θsp is computed. Therefore, accuracy in the measurement of the total reflection attenuation angle θsp can be prevented from being degraded by a difference in sensitivity between photodiodes. Also, the above-described sensitivity correction is made by processing signals in the sensitivity correction part 27, so variable resistors for correction become unnecessary and the correction process can be performed by small and inexpensive correction means. In addition, the pitch between photodiodes is one-fourth or less of the half-value width of a dark line, so the total reflection attenuation angle θsp can be measured with high resolution.

Thereafter, each time a predetermined time elapses, the total reflection attenuation angle θsp is computed, and a quantity of change in angle from the start of measurement is computed and displayed on the display unit 26.

Figure 4A:
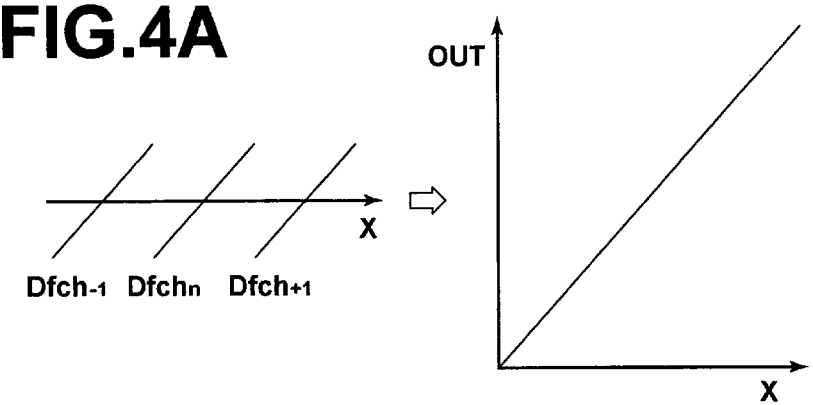
FIGS. 4A and 4B are graphs showing the relationship between the sensitivity characteristic of each light-receiving element and the output characteristic of the signal processing unit.
Figure 4B:
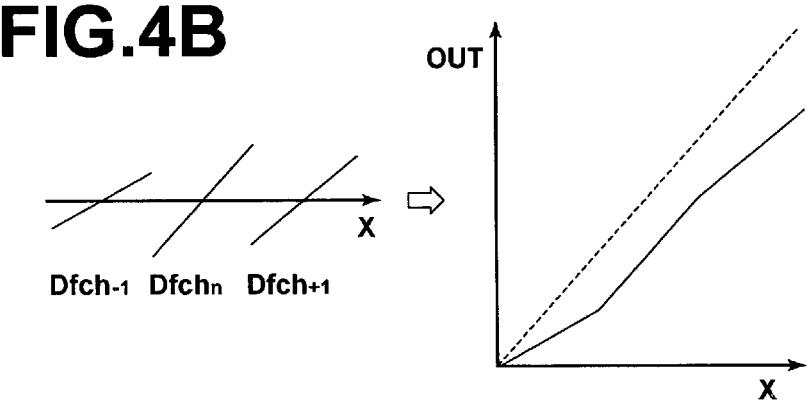

Now, a description will be made of the relationship between the sensitivity characteristic of the photodiodes 23a, 23b, 23c . . . and the computation characteristic for the total reflection attenuation angle θsp of the signal processing unit 25. In FIGS. 4A and 4B, graphs on the left side show the relationship between the position of a dark line and the output characteristic of a differential channel, while graphs on the right side show the relationship between the actual position of a dark line and the position of a computed dark line (total reflection attenuation angle θsp).

FIG. 4A shows the relationship between the actual position of a dark line and the position of a computed dark line in the case where the light-receiving elements are uniform in sensitivity. In this case, the above-described relationship has ideal linearity. As described above, by correcting for the sensitivity of each light-receiving element, the relationship between the actual position of a dark line and the position of a computed dark line can be linearized, but there are cases where strictly speaking, the relationship is not in perfect linearity. In such a case, as shown in FIG. 4B, the computation characteristic varies non-linearly, so that errors will occur in the results of computation of the dark line position.

Figure 5:
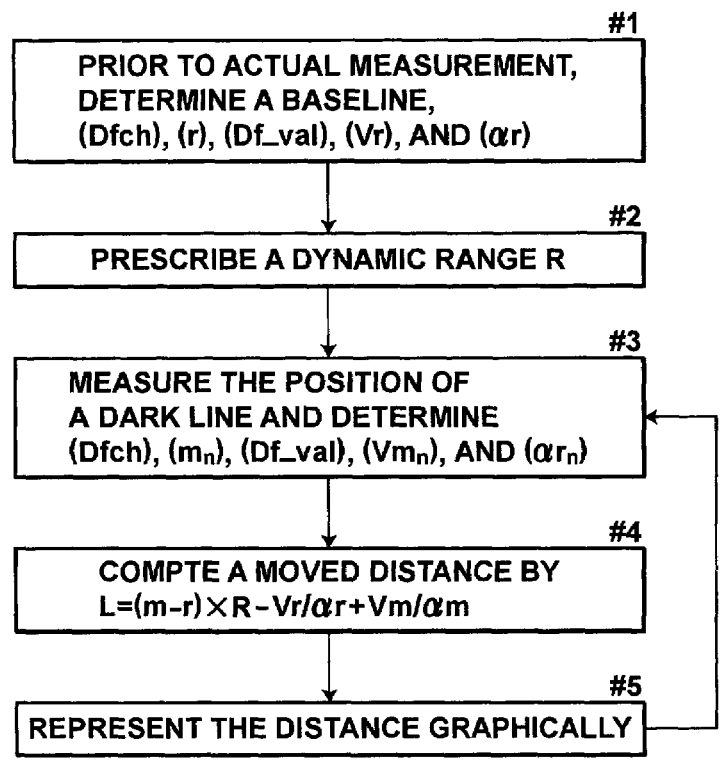
FIG. 5 is a flowchart showing how a dark line is computed.
Figures 6A, 6B:
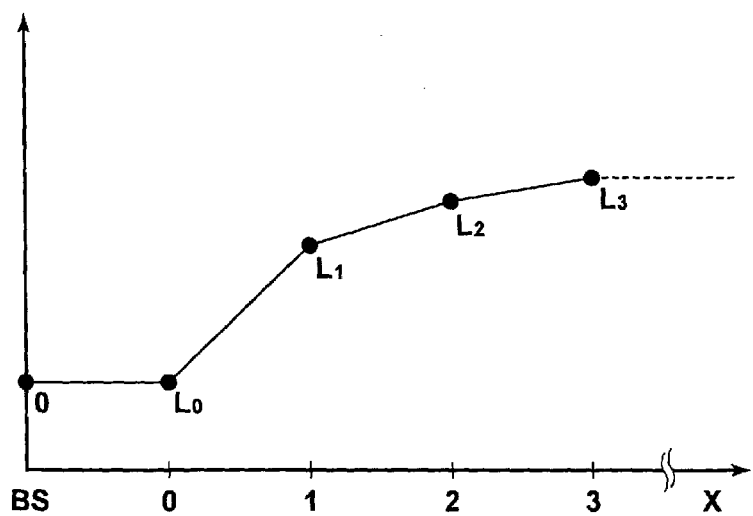
FIGS. 6A and 6B are a table and a graph showing various values obtained by measurements.

To overcome the problem of non-linearity, a description will be given of how a dark line is computed by the computation part 28 of the surface plasmon resonance measuring apparatus of the first embodiment. The dark-line computation process is shown in FIG. 5, and various values obtained by measurements are shown in FIG. 6.

Initially, the position of a dark line computed from the above-described skip difference value is used as a baseline, and the order (r) of arrangement of a differential channel (Dfch) detecting the baseline, the output voltage value (Df_val) Vr of the $r^{th}$ differential channel (Dfch) in pre-measurement, and the differential gradient αr of the $r^{th}$ differential channel (Dfch) in pre-measurement, are determined as reference (step #1). Then, a dynamic range R (width of detection per one difference channel) is prescribed (step #2).

Next, every time a predetermined time elapses, a measurement is made, and the order (m) of arrangement of a differential channel (Dfch) detecting a dark line, the output voltage value (Df_val) Vm of the $m^{th}$ differential channel (Dfch) in actual measurement, and the differential gradient αm of the $m^{th}$ differential channel (Dfch) in actual measurement, are determined (step #3). The moved distance (L) from the baseline is computed from Equation, L=(m−r)×R−Vr/αr+Vm/αm (step #4), and the computed distances (L) are graphed (step #5). The distance (L) computed in step #4 is a value corresponding univocally to the position of a dark line (total reflection attenuation angle θsp), so the dark line position can be computed by the above-described process.

Moreover, in the case of measuring a change in the position of a dark line with the passage of time, the process returns to step #3. In the computation part 28, quantities of change in angle from the start of measurement are graphed, and the obtained graph is displayed on the display unit 26.

If the dielectric constant, that is, refractive index of a substance in contact with the second thin film layer 14 of the measuring chip 10 changes, the total reflection attenuation angle θsp varies with that change. Therefore, by continuously measuring a quantity of change in the total reflection attenuation angle θsp with the passage of time, a change in the refractive index of a substance in contact with the second thin film layer 14 can be examined.

As described above, by multiplying the number of differential channels from a differential channel corresponding to the baseline to a differential channel detecting a dark line by the dynamic range R (width of detection per one differential channel) and computing a distance from the baseline to the dark line, it is possible to compute the position of the dark line accurately without undergoing the influence of the individual difference between the sensitivity characteristics of the light-receiving elements constituting the photodiode array.

In the first embodiment, while a light-receiving element that outputs an optical detection signal having a minimum value is specified as a reference light-receiving element, the present invention is not limited to this embodiment.

For instance, when the outputs of two adjacent light-receiving elements are differentiated in the direction where the elements are arranged, two light-receiving elements whose differentiated value is nearest to 0 may be specified as reference light-receiving elements. In this case, while two light-receiving elements are specified as reference light-receiving elements, the above-described judgement maybe performed on only one of the two, or the above-described judgement may be performed on both light-receiving elements.

Now, a description will be given of a surface plasmon resonance measuring apparatus constructed in accordance with a second embodiment of the present invention. Since the entire construction of the second embodiment is approximately the same as the first embodiment, in FIG. 1, only reference numerals for different parts are given in parentheses.

A signal processing unit 40 controls operation of each part and has a sensitivity correction part 27 and a computation part 41. The sensitivity correction part 27 corrects for the sensitivities of the output signals Sa, Sb, Sc, . . . of a photodiode array 23 digitized. The computation part 41 serially computes an average value of every two photodiodes of the photodiode array 23, also computes a skip difference value F from the average values, and finds a total reflection attenuation angle θsp, based on the skip difference value F.

If measurement is started, a laser light source 21 is driven in response to a command from the signal processing unit 40, and a light beam 20 emitted therefrom strikes the interface 12a between the dielectric block portion 11 and first thin film layer 12 of a measuring chip 10 supplied with a liquid sample 15. The light beam 20 totally reflected at the interface 12a is detected by the photodiode array 23.

The signals Sa, Sb, Sc . . . output from the photodiodes 23a, 23b, 23c . . . of the photodiode 23 are converted into digital signals by an A/D converter 24 and are input to the sensitivity correction part 27, in which a correction process is performed. The corrected signals are output to the computation part 41 as signals Sa', Sb', Sc' . . . shown in FIG. 2C.

Figure 7A:
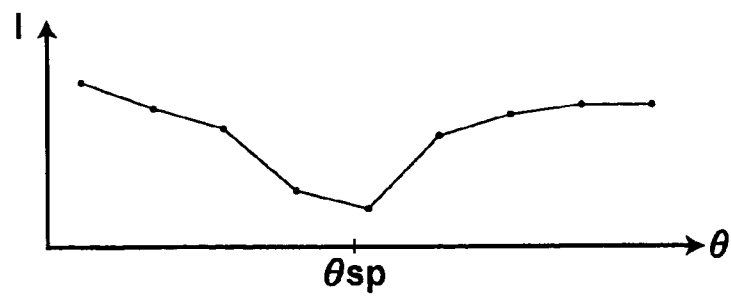
FIG. 7A is a graph showing the relationship between the incidence angle θ of a light beam at an interface and the light intensity I of the light beam reflected at that interface, obtained according to the second embodiment.
Figure 7B:
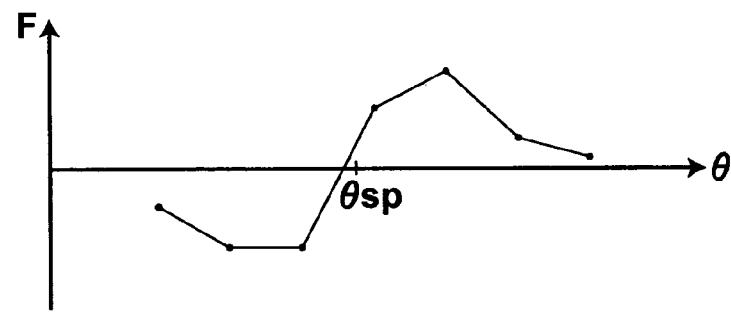
FIG. 7B is a graph showing the relationship between the incidence angle θ and skip difference value F, obtained according to the second embodiment.

In the computation part 28, the photodiodes are first divided into photodiode groups each consisting of two photodiodes, and then computes an average value for each photodiode group. That is, as shown in FIG. 7A, (Sa'+Sb')/2, (Sc'+Sd')/2, (Se'+Sf')/2 . . . are computed. Next, skip difference values F, which are differences between alternate average values, are serially computed. That is, as shown in FIG. 7B, {(Sa'+Sb')/2−(Se'+Sf')/2}, {(Sc'+Sd')/2−(Sg'+Sh')/2} . . . are serially computed. In the second embodiment, while photodiodes are divided into photodiode groups consisting of two photodiodes, the present invention is not limited to this embodiment, but they may be divided into photodiode groups consisting of three or more photodiodes.

Therefore, the computation part 41, as with the first embodiment, computes the total reflection attenuation angle θ sp from the photodiode that has an output near to difference value F=0 corresponding to the total reflection attenuation angle θsp, based on skip difference values F.

As evident in the foregoing description, in the second embodiment, as with the first embodiment, the total reflection attenuation angle θsp is computed based on the skip difference value F that is good in linearity, so the total reflection attenuation angle θsp can be accurately measured. Also, the other advantages of the first embodiment are likewise obtained.

In addition, the second embodiment computes an average value for each photodiode group consisting two adjacent photodiodes, also computes a skip difference value from this average value, and finds the total reflection attenuation angle θsp. Therefore, by computing an average value, noise contained in the photodiode outputs is cancelled and the noise influence is reduced, so that reliability in measuring the total reflection attenuation angle θsp is further enhanced. Instead of an average value for each photodiode group, a total value for each photodiode group may be computed. In this case, a signal value in computing a skip difference value can be made greater. Also, instead of an average value, a value obtained by dividing a total value by a desired value, a value obtained by multiplying a total value by a desired value, etc., may be employed.

Figure 8A:
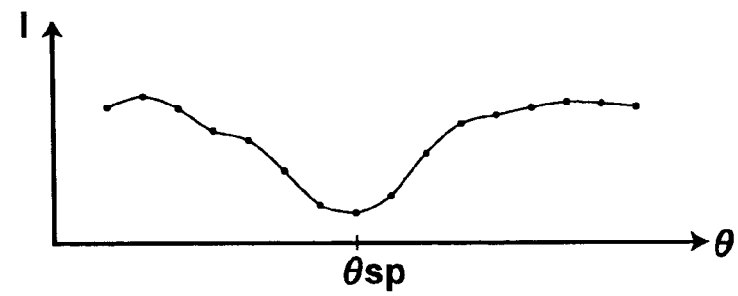
FIG. 8A is a graph showing the relationship between the incidence angle θ and the light intensity I, obtained according to an alteration of the second embodiment.
Figure 8B:
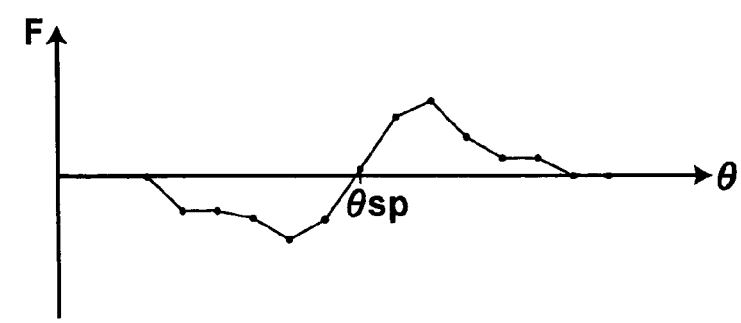
FIG. 8B is a graph showing the relationship between the incidence angle θ and skip difference value F, obtained according to the alteration of the second embodiment.

As an alteration of the second embodiment, there is a surface plasmon resonance measuring apparatus equipped with a signal processing unit 50 (see FIG. 1). The signal processing unit 50 has a sensitivity correction part 27 and a computation part 51. The computation part 51 serially computes an average value of two or more adjacent photodiodes of a photodiode array 23 and computes skip difference values F from the average values. For example, in the computation part 50, an average value of three adjacent photodiodes is first computed. That is, as shown in FIG. 8A, (Sa'+Sb'+Sc')/3, (Sb'+Sc'+Sd')/3, (Sc'+Sd'+Se')/3 . . . are computed. Next, skip difference values F, which are differences between alternate average values, are serially computed. That is, as shown in FIG. 8B, {(Sa'+Sb'+Sc')/3−(Sc'+Sd'+Se')/3}, {(Sb'+Sc'+Sd')/3−(Sd'+Se'+Sf')/3} . . . are serially computed. In this case, (the number of photodiodes—3) average values are computed, so reliability in the results of measurement of the total reflection attenuation angle θsp can be further enhanced while holding high resolution. Instead of an average value of three adjacent photodiodes, a total value of three adjacent photodiodes may be used. In this case, a signal value in computing a skip difference value can be made greater. Also, instead of an average value, a value obtained by dividing a total value by a desired value, a value obtained by multiplying a total value by a desired value, etc., may be employed.

Figure 9:
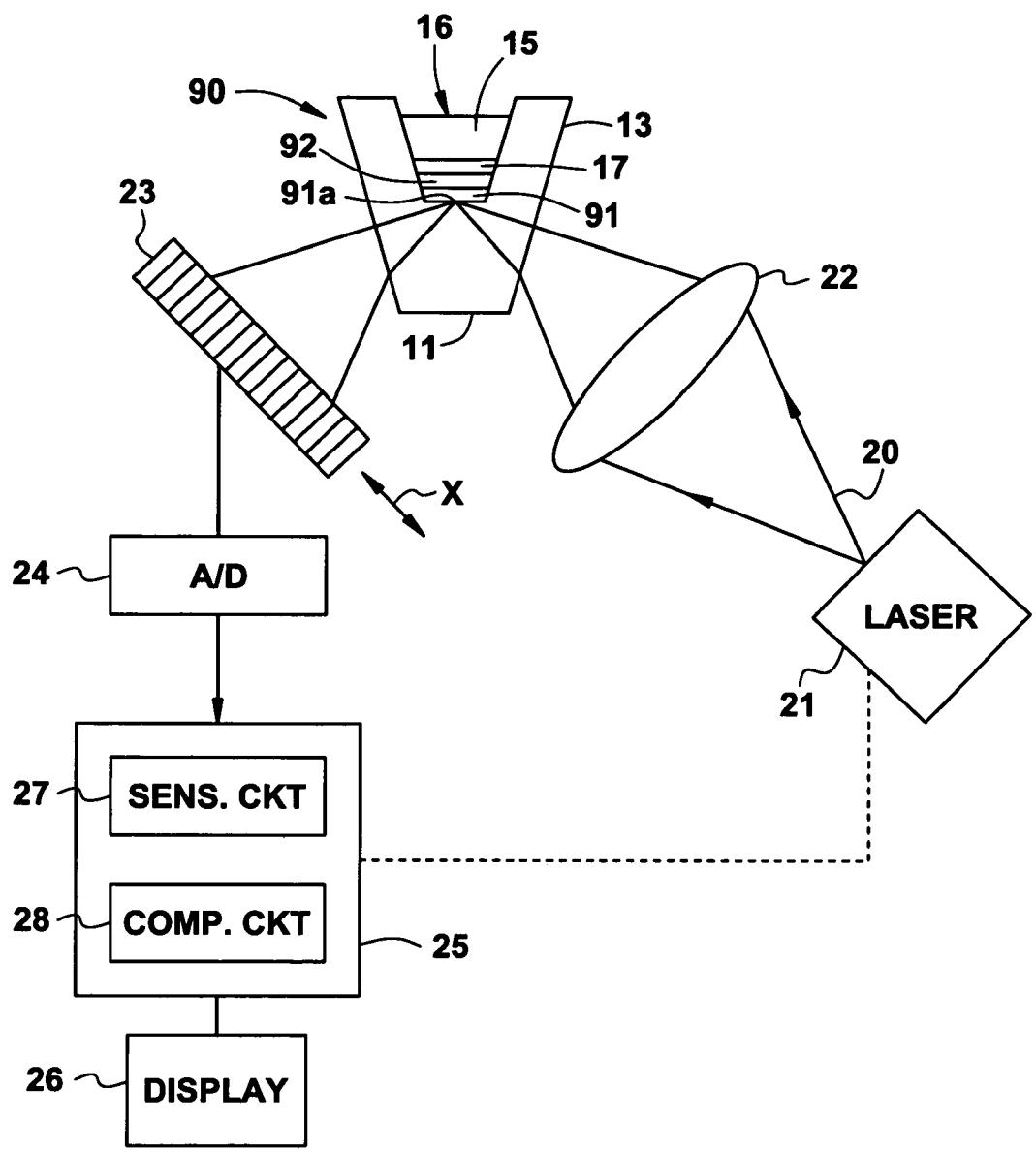
FIG. 9 is a side view showing a leaky mode measuring apparatus constructed in accordance with a third embodiment of the present invention.

Referring to FIG. 9, there is shown a measuring apparatus constructed in accordance with a third embodiment of the present invention. Since the same reference numerals are applied to the same parts as those of FIG. 1, a description of the same parts is omitted unless particularly necessary.

The measuring apparatus of the third embodiment utilizes attenuated total reflection (ATR) and is a leaky mode measuring apparatus previously described. The third embodiment is constructed so that it employs a measuring chip 90. The measuring chip 90 has a cladding layer 91, which is formed on the top surface of a lower dielectric portion 11 and on the interior wall surface of an upper sample holding portion 13. The measuring chip 90 further has an optical waveguide layer 92 formed on the surface of the cladding layer 91.

The dielectric block portion 11 is formed, for example, from synthetic resin, or optical glass such as BK7, etc. The cladding layer 91 is formed into a thin film from a dielectric lower in refractive index than the dielectric block portion 11, or from metal such as gold, etc. The optical waveguide layer 92 is also formed into a thin film from a dielectric higher in refractive index than the cladding layer 91, such as polymethylmethacrylate (PMMA). The film thickness of the cladding layer 91 is 36.5 nm in the case where it is formed from a thin gold film. The film thickness of the optical waveguide layer 92 is about 700 nm in the case where it is formed from PMMA.

In the above-described leaky mode measuring apparatus, if a light beam 20 is emitted from a laser light source 21 and strikes the cladding layer 91 through the dielectric block portion 11 at an incidence angle greater than or equal to a critical angle at which total internal reflection (TIR) occurs, then the light beam 20 is totally reflected at the interface 91a between the dielectric block portion 11 and the cladding layer 91. However, light with a specific wave number, incident on the optical waveguide layer 92 through the cladding layer 91 at a specific incidence angle, propagates in the optical waveguide layer 92 in a waveguide mode. If the waveguide mode is thus excited, the greater part of the incident light is confined within the optical waveguide layer 92, and consequently, attenuated total reflection (ATR) occurs in which the intensity of the light beam 20 totally reflected at the interface 91a drops sharply.

The wave number of the light beam 20 propagating in the optical waveguide layer 92 depends on the refractive index of a sensing substance 17 on the optical waveguide layer 92. Therefore, by knowing the above-described total reflection attenuation angle θsp at which attenuated total reflection (ATR) occurs, the refractive index of the sensing substance 17 can be measured and the coupled state between the protein in the liquid sample 15 and the sensing substance 17 can be measured.

In the third embodiment, as with the first embodiment, the total reflection attenuation angle θsp is computed based on a skip difference value that is good in linearity, so the total reflection attenuation angle θsp can be accurately measured. Also, the other advantages of the first embodiment can be similarly obtained.

In the above-described embodiments, while a difference between the outputs of alternate photodiodes is obtained in computing a skip difference value, the present invention is not limited to this, but a difference may be obtained with the space of two or more photodiodes. It is desirable to set the spacing between photodiodes so that the noise in a signal output from each photodiode or the influence of waveform distortion can be efficiently removed, and compute a skip difference value.

In addition, in the above-described embodiments, although the dielectric block portion and the thin film layers constitute a disposable measuring chip, the same advantages can be obtained, even in the case where the dielectric block portion is incorporated into the main body of the surface plasmon resonance measuring apparatus without being formed as an integrated chip.

While the present invention has been described with reference to the preferred embodiments thereof, the invention is not to be limited to the details given herein, but may be modified within the scope of the invention hereinafter claimed.

What is claimed is:

1. A measuring apparatus comprising:
   a measuring chip comprising
      a dielectric block portion,
      a thin film layer formed on one surface of said dielectric block portion, and
   a sample holding mechanism for holding a sample on a surface of said thin film layer;
   a light source for emitting a light beam;
   an optical incidence system for causing said light beam to enter said dielectric block portion at angles of incidence so that a total internal reflection condition is satisfied at an interface between said dielectric block portion and said thin film layer;
   photodetection means, which comprises a plurality of light-receiving elements, for detecting intensities of said light beam whose incidence angles are different, totally reflected at said interface;
   differentiation means for differentiating an optical detection signal output from each of the light-receiving elements of said photodetection means, in a direction where said light-receiving elements are juxtaposed, at intervals of outputs of two adjacent light-receiving elements; and
   computation means for specifying a reference light-receiving element by a predetermined method, then judging whether or not values of the optical detection signals of a first predetermined number of light-receiving elements increase monotonously in directions going to both sides with said reference light-receiving element as center, and computing a position of a dark line, contained in said light beam reflected at said interface, on the basis of a value obtained by differentiating the outputs of a second predetermined number of light-receiving elements sandwiching said reference light-receiving element when it is judged that the values of the optical detection signals increase monotonously, in said direction where said light-receiving elements are juxtaposed.

2. The measuring apparatus as set forth in claim 1, wherein said predetermined method specifies a light-receiving element, which outputs an optical detection signal having a minimum value, among said plurality of light-receiving elements, as said reference light-receiving element.

3. The measuring apparatus as set forth in claim 1, wherein, when outputs of two adjacent light-receiving elements are differentiated in said direction where said light-receiving elements are juxtaposed, said predetermined method specifies two light-receiving elements whose differentiated value is nearest to 0, as reference light-receiving elements.

4. A measuring apparatus comprising:
   a measuring chip comprising
      a dielectric block portion, a thin film layer formed on one surface of said dielectric block portion, and a sample holding mechanism for holding a sample on a surface of said thin film layer;

a light source for emitting a light beam;

an optical incidence system for causing said light beam to enter said dielectric block portion at angles of incidence so that a total internal reflection condition is satisfied at an interface between said dielectric block portion and said thin film layer;

photodetection means, which comprises a plurality of light-receiving elements, for detecting intensities of said light beam whose incidence angles are different, totally reflected at said interface;

differentiation means for differentiating an optical detection signal output from each of the light-receiving elements of said photodetection means, in a direction where said light-receiving elements are juxtaposed, at intervals of outputs of two adjacent light-receiving elements; and computation means for computing a position of a dark line that is obtained in actual measurement by computing a distance (L) from a predetermined baseline to the position of said dark line, using the following equation:

$$L = (m-r) \times R - Vr/\alpha r + Vm/\alpha m$$

in which R is a dynamic range per one differential channel when one difference channel comprises two adjacent light-receiving elements, r is the order of arrangement of a differential channel corresponding to said predetermined baseline, Vr is a voltage value equivalent to a differentiated value that represents said baseline output by the $r^{th}$ differential channel, $\alpha r$ is the differential gradient of the $r^{th}$ differential channel, m is the order of arrangement of a differential channel that detected the dark line contained in the light beam reflected at said interface, Vm is a voltage value equivalent to a differentiated value output by the $m^{th}$ differential channel, and $\alpha m$ is the differential gradient of the $m^{th}$ differential channel.

5. A measuring apparatus comprising:

a measuring chip comprising a dielectric block portion, a thin film layer formed on one surface of said dielectric block portion, and a sample holding mechanism for holding a sample on a surface of said thin film layer;

a light source for emitting a light beam;

an optical incidence system for causing said light beam to enter said dielectric block portion at angles of incidence so that a total internal reflection condition is satisfied at an interface between said dielectric block portion and said thin film layer;

photodetection means, which comprises a plurality of light-receiving elements, for detecting intensities of said light beam whose incidence angles are different, totally reflected at said interface;

difference means for computing optical detection signals based on outputs of said light-receiving elements and computing a difference between said optical detection signals with the space of at least one light-receiving element in a direction where said light-receiving elements are juxtaposed; and computation means for measuring a state of attenuated total reflection, based on said difference computed by said difference means.

6. The measuring apparatus as set forth in claim 5, wherein said optical detection signal is an average value obtained by dividing said plurality of light-receiving elements into light-receiving element groups containing a predetermined number of light-receiving elements which are at least two adjacent light-receiving elements, and then averaging outputs of the light-receiving elements of each of said light-receiving element groups.

7. The measuring apparatus as set forth in claim 6, wherein said computation means measures said state of attenuated total reflection by measuring a state of the dark line contained in said light beam; and the pitch between said light-receiving elements is one-fourth or less of the half-value width of said dark line.

8. The measuring apparatus as set forth in claim 7, further comprising sensitivity correction means for correcting for a difference in sensitivity between the light-receiving elements of said photodetection means.

9. The measuring apparatus as set forth in claim 8, wherein said sensitivity correction means corrects for a difference in sensitivity between the light-receiving elements of said photodetection means by processing signals.

10. The measuring apparatus as set forth in claim 6, further comprising sensitivity correction means for correcting for a difference in sensitivity between the light-receiving elements of said photodetection means.

11. The measuring apparatus as set forth in claim 10, wherein said sensitivity correction means corrects for a difference in sensitivity between the light-receiving elements of said photodetection means by processing signals.

12. The measuring apparatus as set forth in claim 5, wherein said optical detection signal is an average value obtained by serially computing an average value of at least two adjacent light-receiving elements in said direction where said light-receiving elements are juxtaposed.

13. The measuring apparatus as set forth in claim 12, wherein said computation means measures said state of attenuated total reflection by measuring a state of the dark line contained in said light beam; and the pitch between said light-receiving elements is one-fourth or less of the half-value width of said dark line.

14. The measuring apparatus as set forth in claim 13, further comprising sensitivity correction means for correcting for a difference in sensitivity between the light-receiving elements of said photodetection means.

15. The measuring apparatus as set forth in claim 14, wherein said sensitivity correction means corrects for a difference in sensitivity between the light-receiving elements of said photodetection means by processing signals.

16. The measuring apparatus as set forth in claim 12, further comprising sensitivity correction means for correcting for a difference in sensitivity between the light-receiving elements of said photodetection means.

17. The measuring apparatus as set forth in claim 16, wherein said sensitivity correction means corrects for a difference in sensitivity between the light-receiving elements of said photodetection means by processing signals.

18. The measuring apparatus as set forth in claim 5, wherein said computation means measures said state of attenuated total reflection by measuring a state of the dark line contained in said light beam; and the pitch between said light-receiving elements is one-fourth or less of the half-value width of said dark line.

19. The measuring apparatus as set forth in claim 18, further comprising sensitivity correction means for correcting for a difference in sensitivity between the light-receiving elements of said photodetection means.

20. The measuring apparatus as set forth in claim 19, wherein said sensitivity correction means corrects for a difference in sensitivity between the light-receiving elements of said photodetection means by processing signals.

21. The measuring apparatus as set forth in claim 5, further comprising sensitivity correction means for correcting for a difference in sensitivity between the light-receiving elements of said photodetection means.

22. The measuring apparatus as set forth in claim 21, wherein said sensitivity correction means corrects for a difference in sensitivity between the light-receiving elements of said photodetection means by processing signals.

23. A measuring apparatus according to claim 5, wherein the difference is computed for light receiving element pairs in a linear array of light receiving elements, said pairs arranged in at least one of: an alternating manner where a space intervening between each one of the pair includes one light receiving elements, and a skipping manner where a space intervening between each one of the pair of light receiving elements includes two or more light receiving elements along the linear array.

* * * * *